US010706971B2

(12) United States Patent
Ramaci

(10) Patent No.: US 10,706,971 B2
(45) Date of Patent: Jul. 7, 2020

(54) SYSTEM FOR MANAGEMENT AND INTERVENTION OF NEUROCOGNITIVE RELATED CONDITIONS AND DISEASES

(71) Applicant: Elements of Genius, Inc., Mt. Pleasant, SC (US)

(72) Inventor: Jonathan E. Ramaci, Mt. Pleasant, SC (US)

(73) Assignee: Elements of Genius, Inc., Mt. Pleasant, SC (US)

(*) Notice: Subject to any disclaimer, the term of this patent is extended or adjusted under 35 U.S.C. 154(b) by 5 days.

(21) Appl. No.: 16/053,638

(22) Filed: Aug. 2, 2018

(65) Prior Publication Data

US 2019/0043622 A1 Feb. 7, 2019

Related U.S. Application Data

(60) Provisional application No. 62/540,459, filed on Aug. 2, 2017.

(51) Int. Cl.
*G08B 23/00* (2006.01)
*G16H 80/00* (2018.01)
(Continued)

(52) U.S. Cl.
CPC .......... *G16H 80/00* (2018.01); *A61B 5/0022* (2013.01); *A61B 5/1112* (2013.01);
(Continued)

(58) Field of Classification Search
CPC ..... A61B 5/0022; A61B 5/0205; A61B 5/021; A61B 5/1112; A61B 5/1118;
(Continued)

(56) References Cited

U.S. PATENT DOCUMENTS 10,025,908 B1 * 7/2018 Orellano ................ G16H 40/63
2004/0044516 A1 * 3/2004 Kennewick ............ G10L 15/22
704/5

(Continued)

*Primary Examiner* — Naomi J Small
(74) *Attorney, Agent, or Firm* — Gregory Finch; Finch Paolino, LLC

(57) ABSTRACT

A system and apparatus for the management and intervention of neurocognitive-related conditions and diseases. The intervention may be implemented in the form of a wearable device providing one or more features of medication adherence, voice, data, SMS reminders, alerts, location via SMS, and 911 emergency. The device may function in combination with an application software accessible to multiple clients (users) executable on a remote server to provide patient support of memory, social contact, daily activities, safety as well as support for caregivers, and feedback for healthcare providers in the management of neurocognitive and neurodegenerative conditions, syndromes, and diseases including dementia and AD. Alternative embodiments implementing monitoring and intervention include using mobile apps or voice-controlled speech interface devices to access cloud control services capable of processing automated voice recognition-response and natural language understanding-processing to perform functions and fulfill user requests.

20 Claims, 8 Drawing Sheets

(51) Int. Cl.
*A61B 5/00* (2006.01)
*G06F 3/0482* (2013.01)
*G16H 20/30* (2018.01)
*G06F 16/9032* (2019.01)
*A61B 5/11* (2006.01)
*G16H 50/20* (2018.01)
*G16H 40/63* (2018.01)
*G16H 40/67* (2018.01)
*G16H 40/20* (2018.01)
*G16H 20/10* (2018.01)
*G06F 1/16* (2006.01)
*G08B 21/04* (2006.01)
*A61B 5/0205* (2006.01)
*G10L 15/18* (2013.01)
*G10L 15/22* (2006.01)
*A61B 5/145* (2006.01)
*A61B 5/021* (2006.01)

(52) U.S. Cl.
CPC ............ *A61B 5/4088* (2013.01); *A61B 5/681* (2013.01); *A61B 5/746* (2013.01); *A61B 5/749* (2013.01); *A61B 5/7465* (2013.01); *G06F 1/163* (2013.01); *G06F 3/0482* (2013.01); *G06F 16/90332* (2019.01); *G16H 20/10* (2018.01); *G16H 20/30* (2018.01); *G16H 40/20* (2018.01); *G16H 40/63* (2018.01); *G16H 40/67* (2018.01); *G16H 50/20* (2018.01); *A61B 5/021* (2013.01); *A61B 5/0205* (2013.01); *A61B 5/1118* (2013.01); *A61B 5/14532* (2013.01); *A61B 5/7435* (2013.01); *G08B 21/0423* (2013.01); *G10L 15/18* (2013.01); *G10L 15/22* (2013.01); *G10L 2015/223* (2013.01)

(58) Field of Classification Search
CPC ... A61B 5/14532; A61B 5/4088; A61B 5/681; A61B 5/7435; A61B 5/746; A61B 5/7465; A61B 5/749; G06F 16/90332; G06F 1/163; G06F 3/0482; G08B 21/0423; G10L 15/18; G10L 15/22; G10L 2015/223; G16H 20/10; G16H 20/30; G16H 40/20; G16H 40/63; G16H 40/67; G16H 50/20; G16H 80/00
USPC ...................................................... 340/573.1
See application file for complete search history.

(56) References Cited

U.S. PATENT DOCUMENTS

| | | | | |
|---|---|---|---|---|
| 2008/0294058 | A1* | 11/2008 | Shklarski | A61B 5/02055 600/502 |
| 2014/0371599 | A1* | 12/2014 | Wu | G06T 7/254 600/476 |
| 2015/0363570 | A1* | 12/2015 | Hanina | G06K 9/00771 348/143 |
| 2017/0188979 | A1* | 7/2017 | Volpe | A61B 5/6823 |
| 2017/0220772 | A1* | 8/2017 | Vleugels | G16H 50/70 |
| 2019/0147721 | A1* | 5/2019 | Avitan | G06F 1/163 340/573.1 |

* cited by examiner

SYSTEM FOR MANAGEMENT AND INTERVENTION OF NEUROCOGNITIVE RELATED CONDITIONS AND DISEASES

RELATED APPLICATIONS

This application claims the benefit of U.S. Provisional Application 62/540,459, entitled "ASSISTIVE TECHNOLOGY SYSTEM FOR THE MANAGEMENT AND INTERVENTION OF NEUROCOGNITIVE RELATED CONDITIONS AND DISEASES," filed Aug. 2, 2017 and hereby incorporated by reference.

FIELD

The present disclosure relates to the field of wearable connected systems for healthcare application; in particular, a system and apparatus for the management and intervention of neurocognitive-related conditions and diseases.

BACKGROUND

Dementia is a common and costly neurocognitive degenerative disease characterized by the progressive deterioration of intellectual abilities including memory, learning, comprehension, language, orientation, and judgement. In general, people with dementia (PwD) display a subset of the following symptoms: progressive memory loss, impairment in cognitive function, speech impairments, declined control over focused movements, changes in personality, deterioration in emotional control, social behavior, motivation, and increasing difficulty in carrying out daily living activities. Per the Alzheimer's Association, more than 5 million people are living in the US with AD and by 2050, this number could rise as high as 16 million. In 2017, AD and other dementias will cost the US nation $259 billion. By 2050, these costs could rise as high as $1.1 trillion.

The effects that dementia has on a person's daily life can be placed into four categories: Cognitive (i.e. difficulty in recognizing people and places, remembering details); Functional (i.e. difficulty in completing everyday tasks and activities of independent living, problems following social cues and slowed reactions); Behavioral (i.e. loss of social skills, overly active response to changes or stimuli in the environment, repetitive behavior patterns and inappropriate responses or behaviors); and Psychological (i.e. irritability, mood swings, frustration and anger with self and others, changes in personality, anxiety, and depression) (World Health Organization, 2015; Alzheimer's Disease International, 2015).

Most of the people with dementia live in a community and are supported by both family and friends as well as professional caregivers and services. More than 15 million Americans provide unpaid care for people with AD or other dementias. In 2016, 15.9 million family and friends provided 18.2 billion hours of unpaid assistance to those with Alzheimer's and other dementias, a national contribution value of $230.1 billion. Alzheimer's takes a devastating toll on caregivers in terms of substantial emotional, financial, and physical difficulties and hardship. (Alzheimer's Association, 2017).

Significant challenges and unmet needs exist in assisting PwD during the progression of their disease. Aside from physical problems (i.e. handling objects, loss of eyesight and hearing, incontinence) the most frequently identified unmet needs are in the areas of information (i.e., on the condition, treatment, prognosis, care and support possibilities, care service appointments, etc.), memory problems, communication, and psychological distress (i.e. anxiety). Quality of life (QoL) issues of PwD that have been identified include physical and mental health, social contact with family and friends, being useful to others, sufficient meaningful activities during day time, enjoyment of activities, self-esteem (being respected by others), lack of orientation in space-time, self-determination, safety, and freedom. PwD require reinforcement of identity, episodic memory, assistance against apathy, and most importantly the facilitation of all aspects of communication and motivation to express opinions, thoughts, wishes and fears and reinforcing their feelings of social belongingness. Education, psychological support, engagement with social services and charitable groups are all recommended but are problematic for individuals living alone.

General care and psychosocial measures are the mainstay of care management. Family caregivers, neighbors, and friends can meet some of needs of PwD, while professionals and healthcare providers meet others. Despite the efforts of these informal and formal caregivers, not all the needs of PwD can be met. The reasons for this include the limited time that both informal and formal caregivers have available, and the lack of, or limited availability of professional services tailored specifically to the needs of PwD. Dementia can make it more difficult to communicate with others. As the syndrome progresses, self-expression becomes harder and the decline in the ability to communicate with others leads to isolation. In addition, the needs of the caregiver become increasingly relevant as the disease progresses. The constant pressure to meet their relative's needs for assistance and support can result in debilitating levels of stress for the caregiver, resulting in the affected person's placement into long-term care. Higher caregiver burden is reported with dementia people who either are a spouse, older, or more functionally or behaviorally impaired. From a caregiver's perspective, decreasing the number of interactions required to complete a daily living activity has a direct positive impact on caregiver burden. Even small decreases in caregiver burden have been found to alleviate the prevalence of depressive symptoms in caregivers of individuals with AD. This can lead to more successful informal care, resulting in lower medical costs and delayed long-term care placements. Therefore, combined support programs, focused on the needs of both PwD and caregivers, are more effective.

Products and services have emerged in the market to make to the life of PwD easier as well as help caregivers and family members to take care of them. However, despite all efforts for covering most of PwD sufferers needs, it is challenging to find a means capable of aiding them with daily activities combined with memory reinforcement, enhancement in feeling safe, and maintains their social contacts. In addition, the need for personalized and context-sensitive information is lacking and difficult to obtain for all parties given the personal and contextual factors, such as the symptoms of PwD, the relationship between the caregivers and PwD, caregiver characteristics, utilized coping strategies, and the quality support systems available to the caregivers. The need exists for a more flexible, personalized care, and support that is fully in line with the differing needs of patients, caregivers, healthcare providers, and services.

Various pervasive and assistive technologies ranging from Internet applications, mobile devices to smart homes have been employed to assist and support PwD and caregivers with daily activities, safety, leisure, and providing information. These products include automatic pill dispensers, telephones with the photos of frequently call people, which contribute to the support for memory and social contacts, complex and complete tracking devices, using Global Positioning Systems (GPS), that also assist in locating people with dementia when they happen to "wander." For people in the early stages of dementia who live at home, these technologies are particularly useful for keeping users independent while being socially engaged with others. The beneficial effects of computer systems have been observed on orientation, feelings of anxiety, and independence in patients suffering from AD. Besides this, implementing monitoring technologies and detection devices or alarm systems inside and outside the homes of elderly persons are useful to enhance (perceived) safety and security of the person suffering from dementia as well as caregivers. Internet-based applications designed to provide caregivers with clinical, decision-making, and emotional support have shown to be beneficial both to caregivers and to PwD. While some of these assistive technologies (i.e. digital calendars, reminders, location tracking) are particularly useful, the existing solutions are highly fragmented leading to very low adoption and few widespread acceptances.

Nonetheless, despite all the pervasive healthcare technologies, products, and services, available to enhance and improve the QoL of PwD and caregivers, an integrated solution, at a minimum, capable of: a) supporting symptoms of dementia (the most frequent one being the loss of memory) and intervention; b) facilitating social contact and company; c) supporting daily life activities; and d) health monitoring and perceived safety, is lacking. In addition, family caregivers want information on diagnosis, prognosis, treatment, and instructions to care for their love ones suffering from dementia. The need for support for the symptoms of dementia refers to all types of instrumental support in a person's daily life activities, including support to enhance participation and supervision/guidance, and ideally non-pharmacological interventions (i.e. cognitive stimulation, training, and rehabilitation). The need for social contact and company refers specifically to ways of staying connected with family, friends and the social environment as well as feeling useful. The needs for health monitoring and perceived safety refer to the wish to be cared for and to feel safe during disability and disease progression as well as the comfort of caregivers knowing that their loved ones are safe.

Therefore, the need exists for a pervasive integrated healthcare solution to support PwD, caregivers, and healthcare providers in the management of neurocognitive and neurodegenerative conditions, syndromes, and diseases including dementia and AD. The integrated system should incorporate comprehensive and optimal methods for the support of patient memory, social contact, daily activities, patient safety, support for caregivers, and feedback communication with healthcare providers. Such a system should enable a voluntary, active, and collaborative effort between PwD, health care providers, caregivers, and family members, in a mutually beneficial manner to improve independence, improve QoL, and or slow the progression of symptoms and disease.

Through applied effort, ingenuity, and innovation, Applicant has identified a number of deficiencies and problems with systems and apparatuses for the management of neurocognitive and neurodegenerative conditions, syndromes, and diseases including dementia and AD. Applicant has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In the broadest terms, the invention is a pervasive integrated assistive technology system incorporating one or more computing devices, microcontrollers, memory storage devices, executable codes, methods, software, automated voice recognition-response devices, automated voice recognition methods, natural language understanding-processing methods, algorithms, risk stratification tools, and communication channels for patient memory support, patient social contact support, support of daily activities, patient safety, support for caregivers, and feedback for healthcare providers in the management of neurocognitive and neurodegenerative conditions, syndromes, and diseases including dementia and AD. The invention may be implemented in the form of a wearable device providing one or more features of medication adherence, voice, data, SMS reminders, alerts, location via SMS, and 911 emergency. The device may function in combination with an application software platform accessible to multiple clients (users) executable on one or more remote servers to provide patient and caregivers support and monitoring as well as information for healthcare providers; a cognitive wellness ecosystem. The device may function in combination with one or more remote servers, cloud control services capable of providing automated voice recognition-response, natural language understand-processing, applications for predictive algorithm processing, sending reminders, alerts, sending general and specific information for disease management. One or more components of the mentioned system may be implemented through an external system that incorporates a stand-alone speech interface device in communication with a remote server, providing cloud-based control service, to perform natural language or speech-based interaction with the user. The stand-alone speech interface device listens and interacts with a user to determine a user intent based on natural language understanding of the user's speech. The speech interface device is configured to capture user utterances and provide them to the control service. The control service performs speech recognition-response and natural language understanding-processing on the utterances to determine intents expressed by the utterances. In response to an identified intent, the controlled service causes a corresponding action to be performed. An action may be performed at the controlled service or by instructing the speech interface device to perform a function. The combination of the speech interface device and one or more applications executed by the control service serves as a relational agent. The relational agent provides conversational interactions, utilizing automated voice recognition-response, natural language processing, predictive algorithms, or the like, to perform functions, interact with the user, fulfill user requests, educate, inform, monitor compliance, determine health status, well-being, suggest corrective actions-behaviors, or the like.

In a preferred embodiment, the wearable device's form-factor is a hypoallergenic wrist watch, a wearable mobile phone, incorporating functional features that include, but are not limited to, medication reminders, voice, data, SMS text messaging, fall detection, location-based services, and direct 911 emergency access. In an alternative embodiment, the wearable device's form factor is an ergonomic and attachable-removable to-and-from an appendage or garment of a user as a pendant or the like. The wearable may contain one or more microprocessor, microcontroller, micro GSM/GPRS chipset, micro SIM module, read-only memory device, memory storage device, I-O devices, buttons, display, user interface, rechargeable battery, microphone, CODEC, speaker, wireless transceiver, antenna, accelerometer, vibrating motor(output), preferably in combination, to function fully as a wearable mobile cellular phone. The wearable device enables communication with one or more remote servers capable of providing automated voice recognition-response, natural language understand-processing, predictive algorithm processing, reminders, alerts, general and specific information for disease management. One or more components of the mentioned system may be implemented through an external system that incorporates a stand-alone speech interface device in communication with a remote server, providing cloud-based control service, to perform natural language or speech-based interaction with the user. The wearable device enables the user to access and interact with the said relational agent for patient memory support, patient social contact support, support of daily activities, patient safety, support for caregivers, and feedback for healthcare providers in the management of neurocognitive and neurodegenerative conditions, syndromes, and diseases including dementia and AD.

In another preferred embodiment, the wearable device can communicate with a secured HIPAA-compliant remote server. The remote server is accessible through one or more computing devices, including but not limited to, desktop, laptop, tablet, mobile phone, smart appliances (e.g., smart TVs), or the like. The remote server contains a social support application software that include a database for storing patients and user(s) information. The application software provides a collaborative working environment to enable a voluntary, active, and collaborative effort between patients, health care providers, caregivers, and family members, in a mutually acceptable manner to improve independence, improve QoL of PwD and caregivers, and or slow the progression of symptoms and disease for PwD.

The software environment allows for, but is not limited to, daily tracking of patient location, monitoring medication adherence, storing and tracking health data (e.g., blood pressure, glucose, cholesterol, etc.), sending-receiving text messages, sending-receiving voice messages, sending-receiving videos, streaming instructional videos, scheduling doctor's appointments, patient education information, caregiver education information, feedback to healthcare providers, or the like. The application software can be used to store skills relating to the management of neurocognitive and neurodegenerative conditions, syndromes, and diseases including dementia and AD. The application software may contain functions for predicting patient behaviors, cognitive symptoms, cognitive impairment, cognitive degeneration, suggest corrective actions, functions to perform or teach non-pharmacologic interventions. The application software may interact with an electronic health or medical record system.

In an alternative embodiment, the said secured remote server is accessible using said stand-alone speech interface device or the speech interface is incorporated into one or more smart appliances, or mobile apps, capable of communicating with the same or another remote server, providing cloud-based control service, to perform natural language or speech-based interaction with the user, acting as said relational agent. The relational agent provides conversational interactions, utilizing automated voice recognition-response, natural language learning-processing, perform various functions and the like, to interact with the user, fulfill user requests, educate, monitor compliance, provide one or more skills, ask one or more questions, storing answers, perform predictive algorithms with user responses, determine health status, and well-being, and provide suggestions for corrective actions including instructions for non-pharmacologic interventions.

In yet another embodiment, skills are developed and accessible through the relational agent. These skills include disease specific educational topics, nutrition, instructions for taking medication, skills to improve medication adherence, skills to increase persistence, proprietary developed skills, skills developed by another party, caregiver coping skills, behavioral skills, skills for daily activities, cognitive stimulation skills, cognitive training skills, cognitive rehabilitation skills, skills for caring for PwD, or other skills disclosed in the detail embodiments of the present disclosure.

In yet another embodiment, the user interacts with the relational agent via providing responses or answers to clinically validated questionnaires. The questionnaires enable the monitoring of patient behaviors, cognitive function, compliance, adherence, wellness, PwD and caregiver QoL, or the like. The responses or answers provided to the relational agent serve as input to one or more predictive algorithms to calculate a risk stratification profile. Such a profile can provide an assessment for the need of any intervention required by either the patient, healthcare providers, caregivers, or family members.

In summary, the pervasive integrated assistive technology platform enables a high level of interaction for patients, healthcare providers, caregivers, and family members. The system leverages a voice-controlled empathetic relational agent for patient memory support, patient social contact support, support of daily activities, patient safety, support for caregivers, feedback for healthcare providers, or the like, in the management of neurocognitive and neurodegenerative conditions, syndromes, and diseases including dementia and AD with the goals to improve independence, improve QoL of PwD and caregivers, and or slow the progression of symptoms and disease for PwD.

Still further, an object of the present disclosure is a system for management of neurocognitive and neurodegenerative conditions, syndromes, and diseases comprising a speech interface device operably engaged with a communications network, the speech interface device being configured to receive a voice input from a user, process a voice transmission from the voice input, and communicate the voice transmission over the communications network via at least one communications protocol, the speech interface device having at least one audio output means; and, a remote server being operably engaged with the speech interface device via the communications network to receive the voice transmission, the remote server executing a control service comprising an automated speech recognition function, a natural-language processing function, and one or more application protocols, the control service processing the voice transmission to execute one or more system commands, the one or more system commands comprising communicating a user interaction to the speech interface device, determining a user's health status, fulfilling a user request, executing one or more skills, and communicating with one or more third-party servers.

Another object of the present disclosure is a system for management of neurocognitive and neurodegenerative conditions, syndromes, and diseases comprising a patient interface device operably engaged with a communications network, the patient interface device being configured to receive a voice input from a patient user, process a voice transmission from the voice input, and communicate the voice transmission over the communications network via at least one communications protocol, the patient interface device having at least one audio output means; a remote server being operably engaged with the speech interface device via the communications network to receive the voice transmission, the remote server executing a control service comprising an automated speech recognition function, a natural-language processing function, and one or more application protocols, the control service processing the voice transmission to execute one or more system commands, the one or more system commands comprising communicating a user interaction prompt to the speech interface device, determining patient health status, fulfilling a user request, executing one or more skills, and communicating with one or more third-party servers; and, a non-patient interface device being operably engaged with the remote server via the communications network to receive health status and communications associated with the patient user, the non-patient interface being operable to configure one or more patient care protocols associated with the control service and send one or more communications to the patient interface device.

Yet another object of the present disclosure is a pervasive integrated assistive technology system for enabling a distributed care ecosystem for patients with neurocognitive conditions, comprising a patient interface device operably engaged with a communications network, the patient interface device being configured to receive a voice input from a patient user, process a voice transmission from the voice input, and communicate the voice transmission over the communications network via at least one communications protocol, the patient interface device having at least one audio output means; a remote server being operably engaged with the speech interface device via the communications network to receive the voice transmission, the remote server executing a control service comprising an automated speech recognition function, a natural-language processing function, and one or more application protocols, the control service processing the voice transmission to execute one or more system commands, the one or more system commands comprising communicating a user interaction prompt to the speech interface device, determining patient health status, fulfilling a user request, and communicating with one or more third-party servers; a non-patient interface device being operably engaged with the remote server via the communications network to receive health status and communications associated with the patient user, the non-patient interface device being operable to configure one or more patient care protocols associated with the control service and send one or more communications to the patient interface device; and, a health care provider interface device being operably engaged with the remote server via the communications network to receive health status and communications associated with the patient user, the health care provider interface device being operable to configure one or more patient care protocols associated with the control service and send one or more communications to the patient interface device and the non-patient interface device.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

Embodiments of the present disclosure provide for a pervasive integrated assistive technology platform for the support of patient memory, social contact, daily activities, patient safety, support for caregivers, and feedback communication for healthcare providers in the management of neurocognitive and neurodegenerative conditions, syndromes, and diseases including dementia and AD. In one embodiment, the intervention system comprises a combination of at least one of the following components: communication device; computing device; communication network; remote server; cloud server; cloud application software. The cloud server and service are commonly referred to as "on-demand computing", "software as a service (SaaS)", "platform computing", "network-accessible platform", "cloud services", "data centers", and the like. The cloud server is preferably a secured HIPAA-compliant remote server. In an alternative embodiment, the intervention system comprises a combination of at least one; voice-controlled speech interface device; computing device; communication network; remote server; cloud server; cloud application software. These components are configured to function together to enable a user to interact with a resulting relational agent. In addition, an application software, accessible by the user and others, using one or more remote computing devices, provides an environment, a cognitive wellness ecosystem, for implementing the intervention as to enable a voluntary, active, and collaborative effort between PwD, health care providers, caregivers, and family members, in a mutually acceptable manner to improve patient independence, memory, improve QoL for PwD and caregivers, and or slow the progression of symptoms and disease of PwD.

Figure 1:
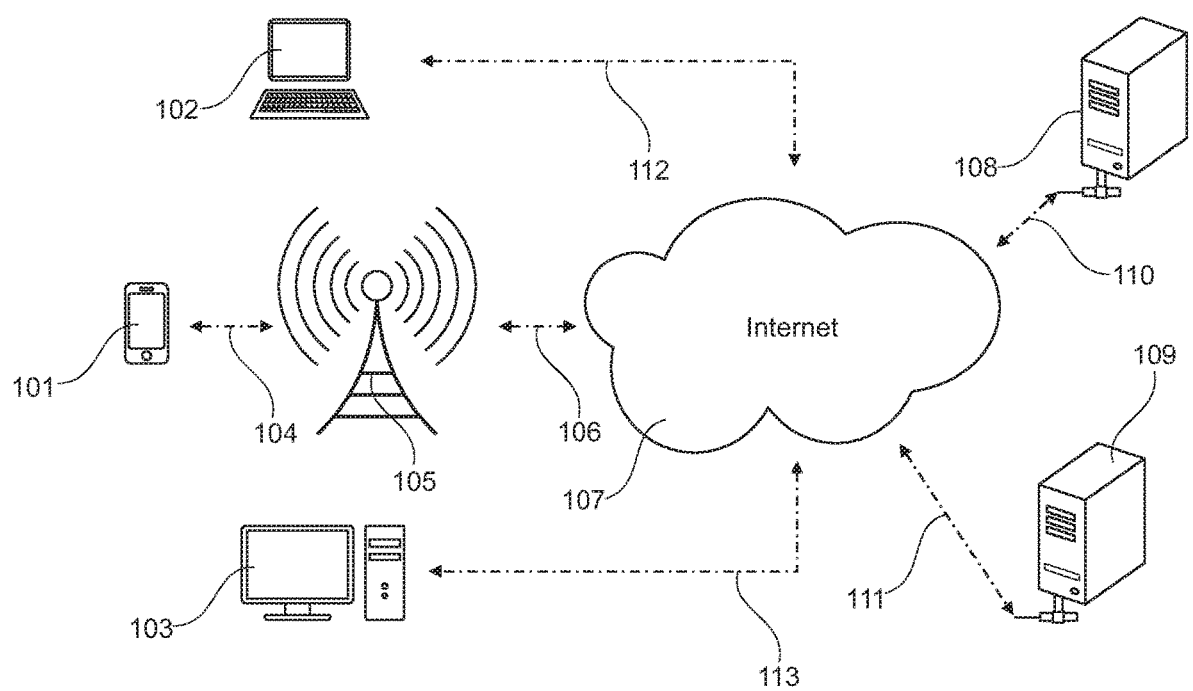
FIG. 1 is a system diagram of the pervasive integrated assistive technology system incorporating a portable mobile device.

FIG. 1 illustrates the pervasive integrated assistive technology system incorporating a portable mobile device 101 for a patient with dementia or the like to interact with one or more remote healthcare provider, caregiver, or family member. One or more users can access the system using a portable computing device 102 or stationary computing device 103. Device 101 communicates with the system via communication means 104 to one or more cellular communication network 105 which can connect device 101 via communication means 106 to the Internet 107. Device 101, 102, and 103 can access one or more remote servers 108, 109 via the Internet 107 through communication means 110 and 111 depending on the server. Device 102 and 103 can access one or more servers through communication means 112 and 113. Computing devices 101, 102, and 103 are preferable examples. However, may be any communication device, including tablet devices, cellular telephones, personal digital assistant (PDA), a mobile Internet accessing device, or other user system including, but not limited to, pagers, televisions, gaming devices, laptop computers, desktop computers, cameras, video recorders, audio/video player, radio, GPS devices, any combination of the aforementioned, or the like. Communication means may comprise hardware, software, communication protocols, Internet protocols, methods, executable codes, instructions, known to one of ordinary skill in the art, and combined so as to establish a communication channel between two or more devices. Communication means are available from one or more manufacturers. Exemplary communication means include wired technologies (e.g., wires, universal serial bus (USB), fiber optic cable, etc.), wireless technologies (e.g., radio frequencies (RF), cellular, mobile telephone networks, satellite, Bluetooth, WIFI, etc.), or other connection technologies. Embodiments of the present disclosure may incorporate any type of communication network to implement one or more communications protocols of the disclosed system, including data and/or voice networks, and may be implemented using wired infrastructure (e.g., coaxial cable, fiber optic cable, etc.), a wireless infrastructure (e.g., RF, cellular, microwave, satellite, Bluetooth, WIFI, etc.), and/or other connection technologies.

Figure 2:
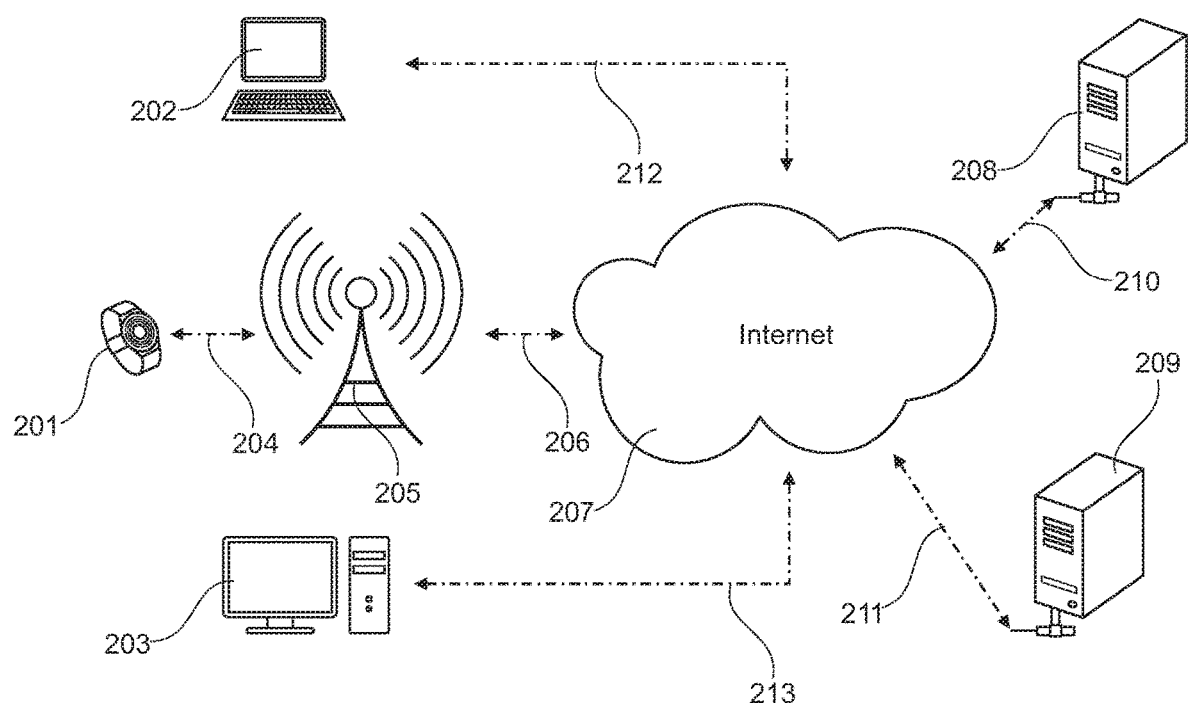
FIG. 2 is a system diagram of the pervasive integrated assistive technology system incorporating a wearable mobile device.

FIG. 2 illustrates the pervasive integrated assistive system incorporating a wearable device 201 for a patient with dementia or the like to interact with one or more remote healthcare provider, caregiver, or family member. In a similar manner as illustrated in FIG. 1, one or more user can access the system using a portable computing device 202 or stationary computing device 203. Computing device 202 may be a laptop used by a family member or caregiver. Stationary computing device 203 may reside at the facility of a healthcare provider (i.e., physician's office). Device 201 communicates with the system via communication means 204 to one or more cellular communication network 205 which can connect device 201 via communication means 206 to the Internet 207. Device 201, 202, and 203 can access one or more remote servers 208, 209 via the Internet 207 through communication means 210 and 211 depending on the server. Device 202 and 203 can access one or more servers through communication means 212 and 213.

Figure 3:
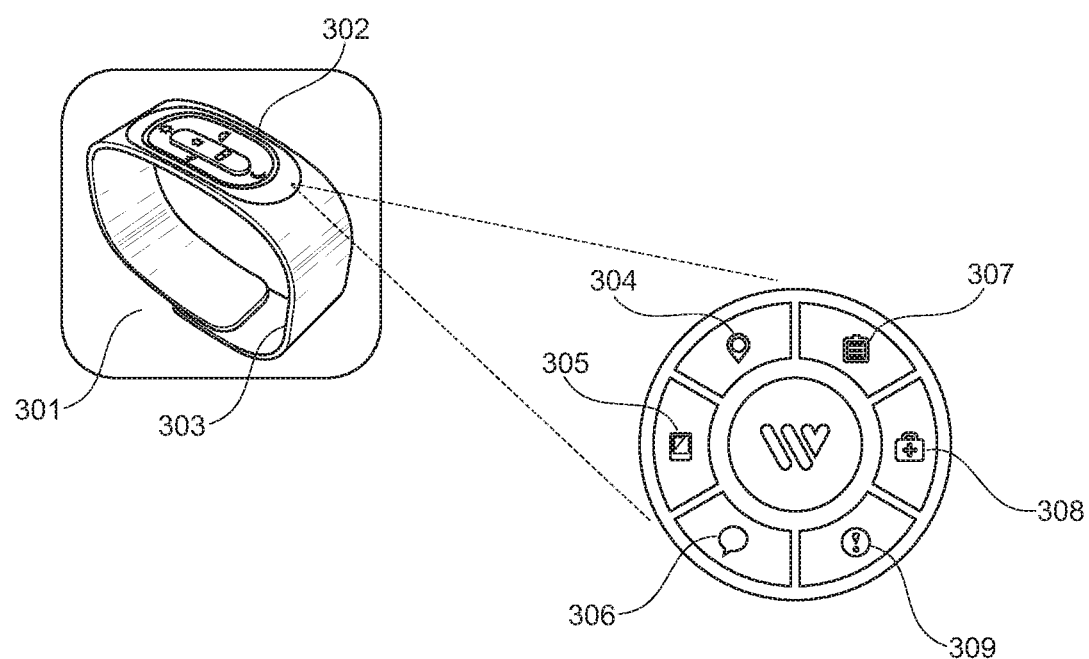
FIG. 3 is a perspective view of a wearable device and key features.

FIG. 3 is a pictorial rendering of the form-factor of a wearable device 301 as a wrist watch as a component of the pervasive integrated assistive technology system. The wearable device 301 is a fully functional mobile communication device (e.g., mobile cellular phone) that can be worn on the wrist of a user. The wearable device 301 comprises a watch-like device 302 snap-fitted onto a hypoallergenic wrist band 303. The watch-like device 302 provides a user-interface that allows a user to access features that include smart and secure location-based services 304, mobile phone module 305, voice and data 306, advanced battery system and power management 307, direct 911 access 308, and fall detection accelerometer sensor 309. The wearable device may contain one or more microprocessor, microcontroller, micro GSM/GPRS chipset, micro SIM module, read-only memory device, memory storage device, I-O devices, buttons, display, user interface, rechargeable battery, microphone, CODEC, speaker, wireless transceiver, antenna, accelerometer, vibrating motor, preferably in combination, to function fully as a wearable mobile cellular phone. A patient with dementia or the like may use wearable device 301, depicted as device 201 of FIG. 2, to communicate with one or more healthcare provider, caregiver, or family member. The wearable device 301 may allow a patient to access one or more remote cloud servers to communicate with a relational agent.

Figure 4:
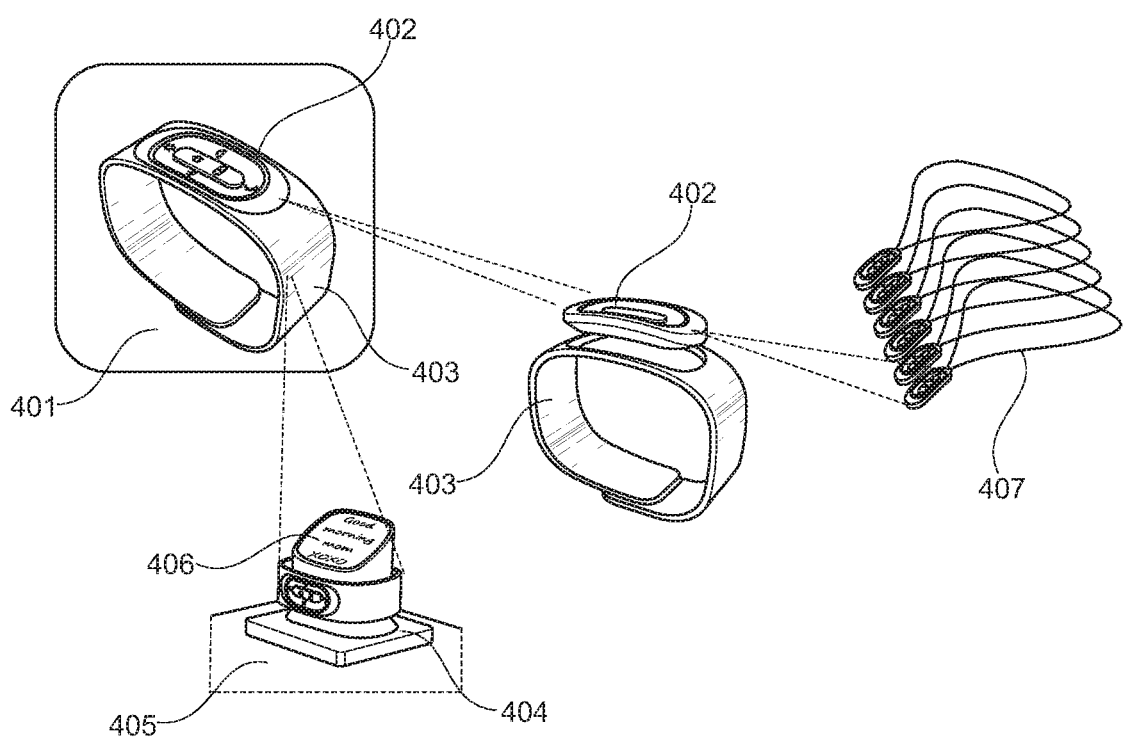
FIG. 4 depicts an alternate wearing option and charging function.

FIG. 4 illustrates details on additional features of the preferred wearable device. Wearable device 401 comprises a watch-like device 402 and wrist band 403, depicted in FIG. 3 as wearable device 301. Wearable device 401 can be stored together with a base station 404 and placed on top of platform 405. Platform 405 may be the surface of any furniture including a night stand. Base station 404 contains electronic hardware, computing devices, and software to perform various functions, for example to enable the inductive charging of the rechargeable battery of wearable device 401, among others. Base station 404 also has a user interface 406 that can display visual information or provide voice messages to a user. Information can be in the form of greetings, reminders, phone messages, or the like. Watch-like device 402 is detachable from wrist band 403 and can be attached to band 407 to be worn by a user as a necklace.

The pervasive integrated assistive technology system of this invention utilizes an application software platform to create an ecosystem for patient memory support, patient social contact support, support of daily activities, patient safety, support for caregivers, and feedback for healthcare providers in the management of neurocognitive and neurodegenerative conditions, syndromes, and diseases including dementia and AD. The application software platform is stored in one or more servers 108, 109, 208, 209 as illustrated in FIG. 1, FIG. 2. The application software platform is accessible to users through one or more computing devices such as device 101, 102, 103, 201, 202, 203 described in this invention. Users of the application software can interact with each other via the said communication means. The software environment allows for, but is not limited to, daily tracking of patient location (e.g., useful when PwD wander), monitoring medication adherence, storing and tracking health data (e.g., blood pressure, glucose, cholesterol, etc.), sending-receiving text messages, sending-receiving voice messages, sending-receiving videos, streaming instructional videos, scheduling doctor's appointments, patient education information, caregiver education information, feedback communication to healthcare providers, and the like. The application software can be used to store skills relating to the management of neurocognitive and neurodegenerative conditions, syndromes, and diseases including dementia and AD. The application software may contain functions for predicting patient behaviors, cognitive symptoms, cognitive impairment, cognitive degeneration, suggest corrective actions, functions to perform or teach non-pharmacologic interventions. The application software may interact with an electronic health or medical record system.

Figure 5:
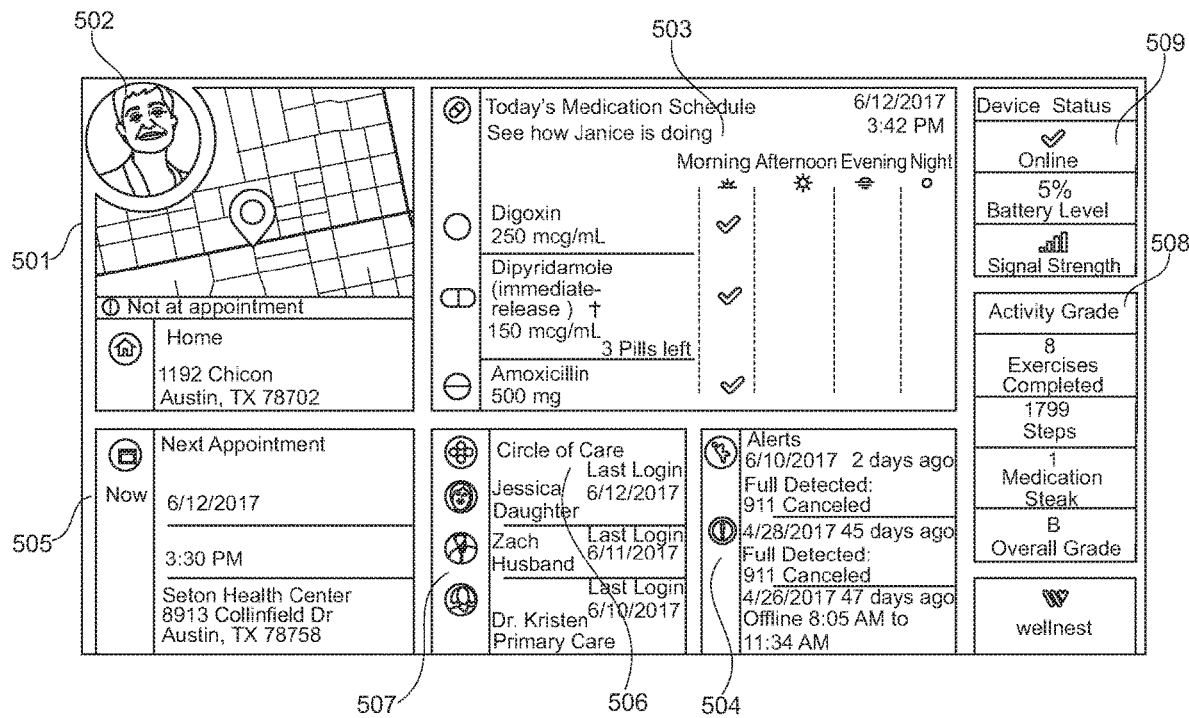
FIG. 5 is a graphical user interface containing the features of an application software platform providing a cognitive wellness ecosystem for implementing the pervasive assistive technology system.

FIG. 5 is a screen-shot 501 that illustrates the type of information that users can generate using the application software platform. Screen-shot 501 provides an example of the information arranged in a specific manner and by no means limits the potential alternative or additional information that can be made available and displayed by the application software. In this example, a picture of patient 502 is presented at the upper left corner. The application may display the current location of patient 502, providing real-time location to allow caregivers to find loved ones when they wander as well as alleviate daily concerns while apart from the patient. A Medication Schedule 503 is available for review and contains a list of medications, dosage, and time when taken. This may be useful for caregivers and healthcare providers in the monitoring of patient compliance. An Alerts 504 is also visible that documents fall detection events and 911 emergency connections for patient 502. The user can review the Next Appointment 505 information. A Circle of Care 506 has pictures of the people 507 (i.e., family members) interacting with patient 502 in this wellness ecosystem and log-in information. A feature can be implemented for picture dialing that is especially useful for PwD. There's also an Activity Grade 508 that allows users to monitor, for example, the physical activities of patient 502. Lastly, but not least, Device Status 509 provides information on the status of said wearable device, described for example in FIG. 3, as wearable device 301.

Figure 6:
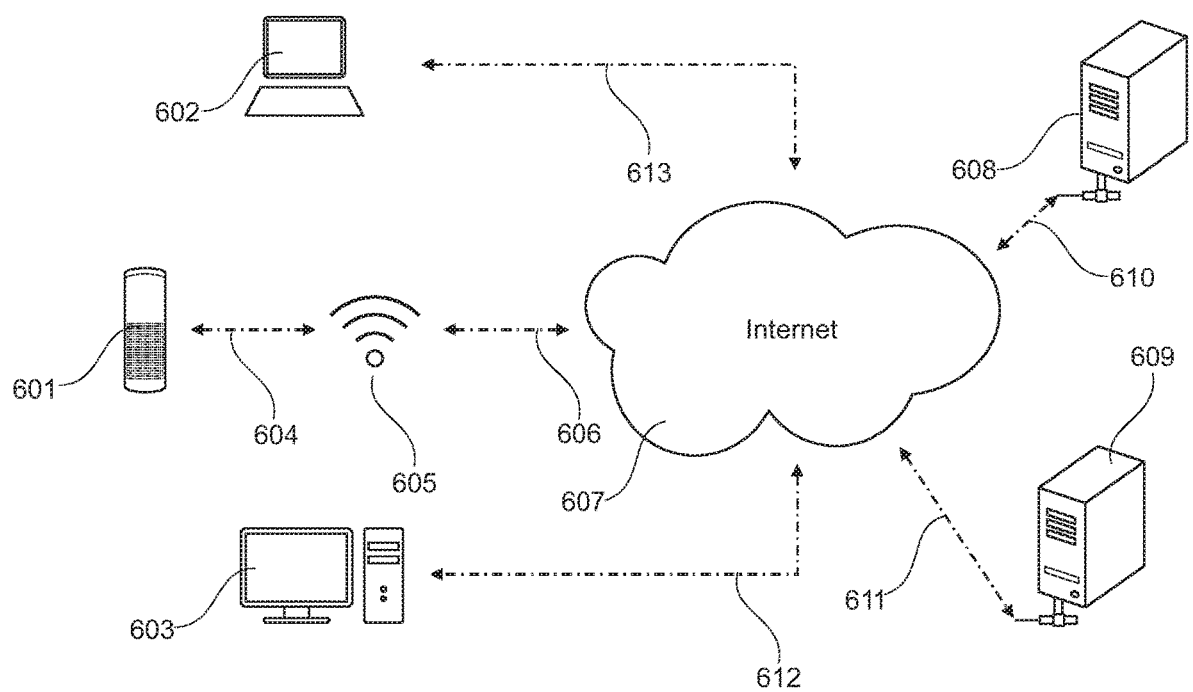
FIG. 6 depicts a graphical user interface of the application software platform accessed through a multimedia player-television using a voice-activated speech interface remote controlled device.

FIG. 6 illustrates the pervasive integrated assistive technology system incorporating a stand-alone voice-activated speech interface device 601 for a patient to interact with one or more remote healthcare provider, caregiver, or family member through a relational agent. In a similar manner as illustrated in FIG. 1, one or more user can access the system using a portable computing device 602 or stationary computing device 603. Computing device 602 may be a laptop used by a family member. Stationary computing device 603 may reside at the facility of a healthcare provider (e.g., physician's office). Device 601 communicates with the system via communication means 604 to one or more WIFI communication network 605 which can connect device 601 via communication means 606 to the Internet 607. Device 601, 602, and 603 can access one or more remote servers 608, 609 via the Internet 607 through communication means 610 and 611 depending on the server. Device 602 and 603 can access one or more servers through communication means 612 and 613. A user may request device 601 to call a family or a health care provider. Exemplary stand-alone speech interface devices with intelligent voice AI capabilities include: Echo, Dot, and Show; all available from Amazon (Seattle, Wash.); Siri, Duplex, Home available from Google, Inc. (Mountain View, Calif.); Cortana available from Microsoft, Inc. (Redmond, Wash.); or the like.

In a preferred embodiment, the said stand-alone device 601 enables communication with one or more remote servers, for example server 608, capable of providing cloud-based control service, to perform natural language or speech-based interaction with the user. The stand-alone speech interface device 601 listens and interacts with a user to determine a user intent based on natural language understanding of the user's speech. The speech interface device 601 is configured to capture user utterances and provide them to the control service located on server 608. The control service performs speech recognition-response and natural language understanding-processing on the utterances to determine intents expressed by the utterances. In response to an identified intent, the controlled service causes a corresponding action to be performed. An action may be performed at the control service or by instructing the speech interface device 601 to perform a function. The combination of the speech interface device 601 and control service located on remote server 608 serves as a relational agent. The relational agent provides conversational interactions, utilizing automated voice recognition-response, natural language processing, predictive algorithms, and the like, to perform functions, interact with the user, fulfill user requests, educate, monitor compliance, determine health status, well-being, suggest corrective actions-behaviors, or the like. The relational agent may fulfill specific requests including calling a family member, a healthcare provider, or arrange a ride share service (e.g., Uber, etc.) for the user. In an emergency, the relational agent may contact an emergency service. Ultimately the said device 601 enables the user to access and interact with the said relational agent to provide support of patient memory, social contact, daily activities, patient safety, support for caregivers, and feedback communication for healthcare providers in the management of neurocognitive and neurodegenerative conditions, syndromes, and diseases including dementia and AD. The information generated from the interaction of the user and the relational agent can be captured and stored in a remote server, for example remote server 609. This information may be incorporated into the application software as described in FIG. 5, making it accessible to multi-users of the ecosystem of cognitive wellness of this invention.

Figure 7:
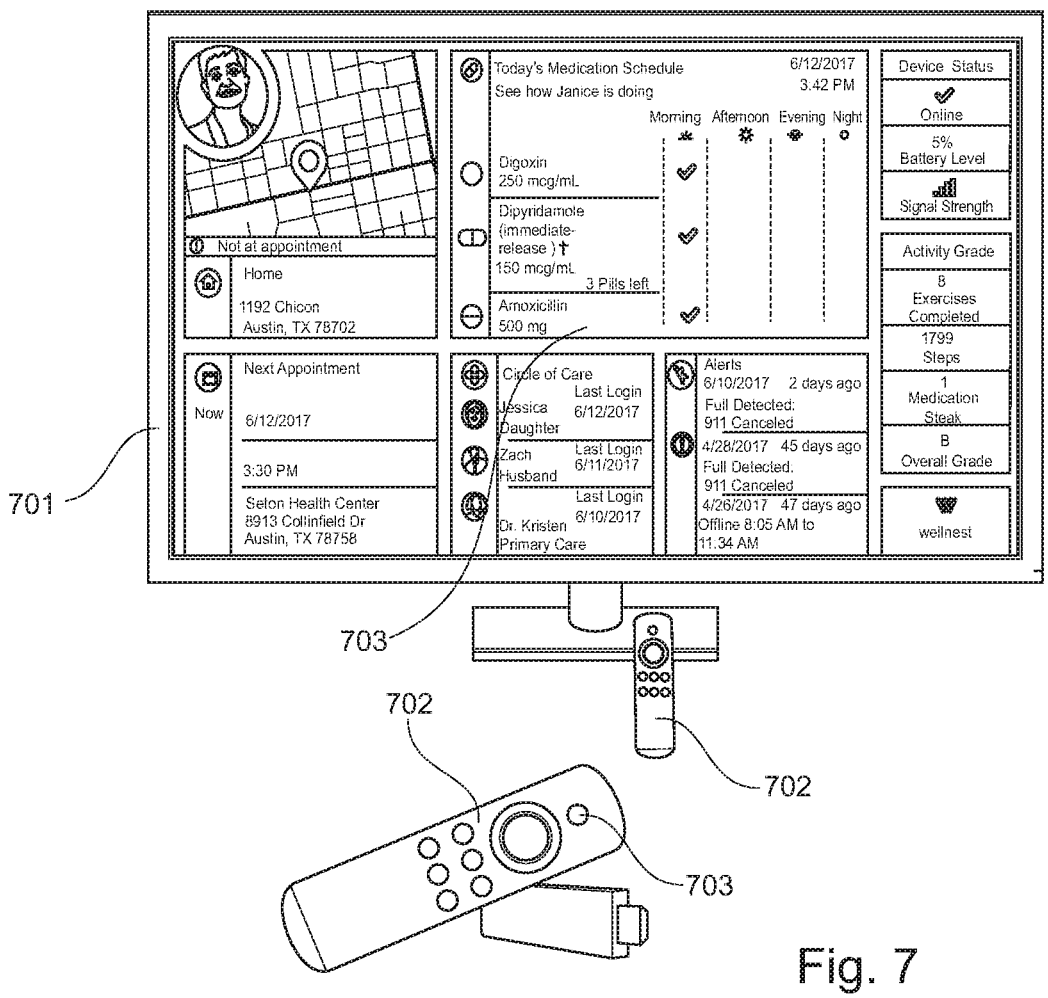
FIG. 7 illustrates the pervasive integrated assistive technology system incorporating a multimedia device; and, FIG. 8 is a function block diagram of the elements of a relational agent.

FIG. 7 illustrates the pervasive integrated assistive technology system incorporating a multimedia device 701 for a dementia patient or the like to interact with one or more remote healthcare provider, caregiver, or family member through a relational agent. In a similar manner as illustrated in FIG. 6, one or more user can access the system using a remote-controlled device 702 containing a voice-controlled speech user interface 703. The multimedia device 701 is configured in a similar manner as device 601 of FIG. 6 as to enable a user to access application software platform depicted by screen-shot 704. The multimedia device 701 may be configured with hardware and software that enable streaming videos to be displayed. Exemplary products include FireTV, Fire HD8 Tablet, Echo Show; products available from Amazon.com (Seattle, Wash.), Nucleus (Nucleuslife.com), Triby (Invoxia.com), TCL Xcess, or the like.

In an alternative embodiment, the function of the relational agent can be accessed through a mobile app and implemented through a system illustrated in FIG. 1. Such mobile app provides access to a remote, for example remote server 108 of FIG. 1, capable of providing cloud-based control service, to perform natural language or speech-based interaction with the user. The mobile app contained in mobile device 101 monitors and captures voice commands and or utterances and transmits them through the said communication means to the control service located on server 108. The control service performs speech recognition-response and natural language understanding-processing on the utterances to determine intents expressed by the utterances. In response to an identified intent, the control service causes a corresponding action to be performed. An action may be performed at the control service or by responding to the user through the mobile app. The control service located on remote server 108 serves as a relational agent. The relational agent provides conversational interactions, utilizing automated voice recognition-response, natural language processing, predictive algorithms, or the like, to perform functions, interact with the user, fulfill user requests, educate, monitor compliance, determine health status, well-being, suggest corrective actions-behaviors, or the like. Ultimately the said device 101 enables the user to access and interact with the said relational agent for the management of neurocognitive and neurodegenerative conditions, syndromes, and diseases including dementia and AD. The information generated from the interaction of the user and the relational agent can be captured and stored in a remote server, for example remote server 109. This information may be incorporated into the application software as described in FIG. 5, making it accessible to multi-users of the ecosystem of cognitive wellness of this invention.

Figure 8:
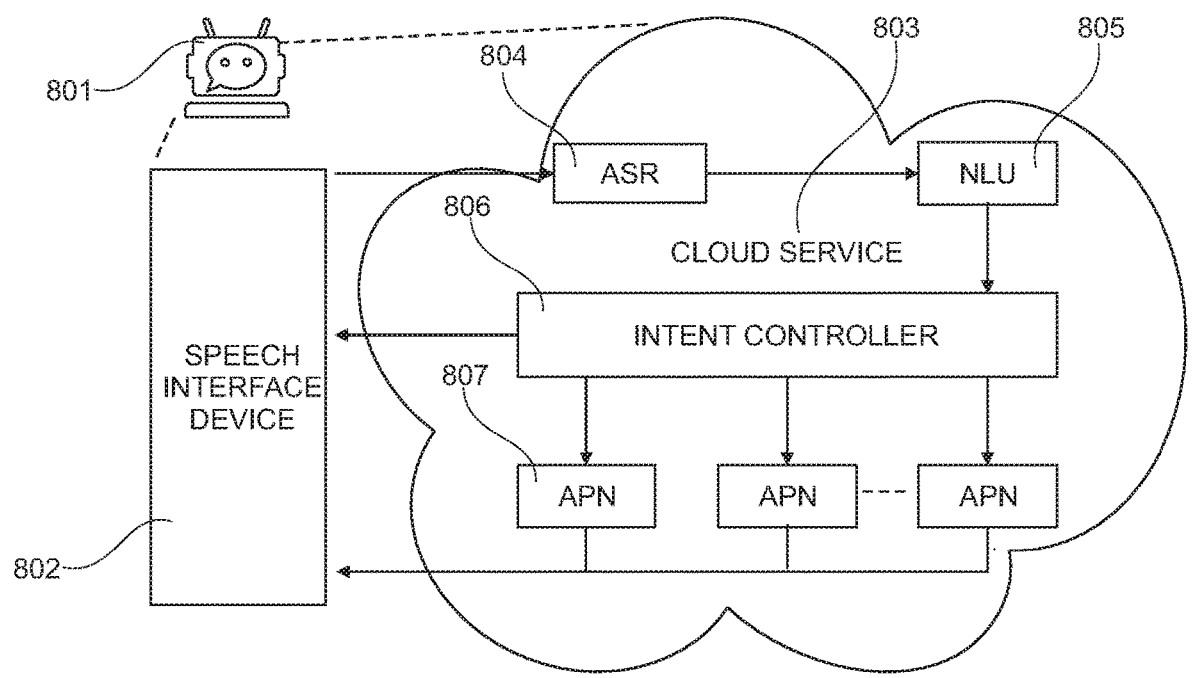

FIG. 8 illustrates a figurative relational agent 801 comprising the voice-controlled speech interface device 802 and a cloud-based control service 803. A representative cloud-based control service can be implemented through a SaaS model or the like. Model services include, but are not limited to: Amazon Web Services, Amazon Lex, Amazon Lambda, available through Amazon (Seattle, Wash.); Cloud AI, Google Cloud available through Google, Inc. (Mountain View, Calif.); Azure AI available through Microsoft, Inc. (Redmond, Wash.); or the like. Such a service provides access to one or more remote servers containing hardware and software to operate in conjunction with said voice-controlled speech interface device, app, or the like. Without being bound to a specific configuration, said control service may provide speech services implementing an automated speech recognition (ASR) function 804, a natural language understanding (NLU) function 805, an intent router/controller 806, and one or more applications 807 providing commands back to the voice-controlled speech interface device, app, or the like. The ASR function can recognize human speech in an audio signal transmitted by the voice-controlled speech interface device received from a built-in microphone. The NLU function can determine a user intent based on user speech that is recognized by the ASR components. The speech services may also include speech generation functionality that synthesizes speech audio. The control service may also provide a dialog management component configured to coordinate speech dialogs or interactions with the user in conjunction with the speech services. Speech dialogs may be used to determine the user intents using speech prompts. One or more applications can serve as a command interpreter that determines functions or commands corresponding to intents expressed by user speech. In certain instances, commands may correspond to functions that are to be performed by the voice-controlled speech interface device and the command interpreter may in those cases provide device commands or instructions to the voice-controlled speech interface device for implementing such functions. The command interpreter can implement "built-in" capabilities that are used in conjunction with the voice-controlled speech interface device. The control service may be configured to use a library of installable applications including one or more software applications or skill applications of this invention. The control service may interact with other network-based services (e.g., Amazon Lambda, etc.) to obtain information, access additional database, application, or services on behalf of the user. A dialog management component is configured to coordinate dialogs or interactions with the user based on speech as recognized by the ASR component and or understood by the NLU component. The control service may also have a text-to-speech component responsive to the dialog management component to generate speech for playback on the voice-controlled speech interface device. These components may function based on models or rules, which may include acoustic models, specify grammar, lexicons, phrases, responses, and the like created through various training techniques. The dialog management component may utilize dialog models that specify logic for conducting dialogs with users. A dialog comprises an alternating sequence of natural language statements or utterances by the user and system generated speech or textual responses. The dialog models embody logic for creating responses based on received user statements to prompt the user for more detailed information of the intents or to obtain other information from the user. An application selection component or intent router identifies, selects, and/or invokes installed device applications and/or installed server applications in response to user intents identified by the NLU component. In response to a determined user intent, the intent router can identify one of the installed applications capable of servicing the user intent. The application can be called or invoked to satisfy the user intent or to conduct further dialog with the user to further refine the user intent. Each of the installed applications may have an intent specification that defines the serviceable intent. The control service uses the intent specifications to detect user utterances, expressions, or intents that correspond to the applications. An application intent specification may include NLU models for use by the natural language understanding component. In addition, one or installed applications may contain specified dialog models for that create and coordinate speech interactions with the user. The dialog models may be used by the dialog management component in conjunction with the dialog models to create and coordinate dialogs with the user and to determine user intent either before or during operation of the installed applications. The NLU component and the dialog management component may be configured to use the intent specifications of the applications either to conduct dialogs, to identify expressed intents of users, identify and use the intent specifications of installed applications, in conjunction with the NLU models and dialog modes, to determine when a user has expressed an intent that can be serviced by the application, and to conduct one or more dialogs with the user. As an example, in response to a user utterance, the control service may refer to the intent specifications of multiple applications, including both device applications and server applications, to identify a "Wellnest" intent. The service may then invoke the corresponding application. Upon invocation, the application may receive an indication of the determined intent and may conduct or coordinate further dialogs with the user to elicit further intent details. Upon determining sufficient details regarding the user intent, the application may perform its designed functionality in fulfillment of the intent. The voice-controlled speech interface device in combination with one or more functions 804,805,806 and applications 807 provided by the cloud service represents the relational agent 801 of the invention.

In a preferred embodiment, skills are developed for the relational agent 801 of FIG. 8 and stored as accessible applications within the cloud service 803. The skills contain information that enables the relational agent to respond to intents by performing an action in response to a natural language user input, information of utterances, spoken phrases that a user can use to invoke an intent, slots or input data required to fulfill an intent, and fulfillment mechanisms for the intent. These application skills may also reside in an alternative remote service, remote database, the Internet, or the like, and yet accessible to the cloud service 803. These skills may include but are not limited to intents for general topics, weather, news, music, pollen counts, UV conditions, patient engagement skills, disease specific educational topics, nutrition, instructions for taking medication, prescription instructions, medication adherence, persistence, coping skills, behavioral skills, risk stratification skills, daily activity, cognitive stimulation, cognitive training, cognitive rehabilitation, or the like. The skills enable the relational agent 801 to respond to intents and fulfill them through the voice-controlled speech interface device. These skills may be developed using application tools (e.g., Amazon Web Services, Alexa Skill Kits; Cloud AI; Azure AI; etc.) from vendors providing cloud control services. The patient preferably interacts with relational agent 801 using skills that enable a voluntary, active, and collaborative effort between patients, health care providers, caregivers, and family members, in a mutually acceptable manner to improve patient independence, improve memory, improve QoL, and or slow the progression of symptoms and disease.

Exemplary skills accessible to a patient may be one or more non-pharmacological interventions including cognitive stimulation, training, and rehabilitation. It is one object of this invention to provide a relational agent with skills to be able to fulfill one or more intents invoked by a patient, for example cognitive stimulation. Cognitive stimulation can be defined as an engagement in a range of activities and discussions aimed at general enhancement of cognitive and social functioning. It is a preferred object to utilize the spoken language interface as a natural means of interaction between the users and the system. Users can speak to the assistive technology similarly as they would normally speak to a human. It is understood, but not bound by theory, that verbal communication accompanied by the opportunity to engage in meaningful conversations can improve language dimension in a cognitive area. As the language dimension improves, communication between the person with dementia and the relational agent will improve subsequently. Improvement in communication of thoughts and feelings might serve as an indicator of changes in QoL following improvement in cognitive function. The relational agent may be used to engage patients in activities aimed at stimulating cognitive and social functioning (e.g., quizzes, memory activities or conversations about childhood). These skills may include: new ideas; thoughts and associations; using orientation and reminiscence as an aid to the here-and-now; providing triggers to aid recall; stimulating language; stimulating executive functioning; and skills to create a patient-centered environment (e.g., providing feeling of uniqueness, individual personalities and preferences). Additional skills can be created to use one or music libraries, preferably in combination with pictures and or videos to stimulate physical activity, evoke positive moods and emotions, support social interaction and stimulate self-disclosure, while reducing anxiety and cognitive symptoms and negative behaviors including wandering, agitation, apathy and sleep disturbances. Others include sorting activities, name recall, proverbs, or the like.

It is also an object of the present invention to provide a means to monitor the well-being of caregivers. This may be implemented using clinically validated questionnaires conducted by the relational agent. Upon a user intent, the relational agent can execute an algorithm or a pathway consisting of a series of questions that proceed in a state-machine manner, based upon YES or NO responses, or specific response choices provided to the user. For example, a clinically validated structure multi-item questionnaire scale may be used to measure the QoL of caregivers. The scale is preferably numerical, qualitative or quantitative, and allows for concurrent and predictive validity, with high internal consistency (i.e., high Cronbach's alpha), high sensitivity and specificity. An example of a measure of QoL might contain a scale with the following questions:

How often does caring for your loved one with dementia negatively affect your relationships with family and or friends?

How often do you experience a conflict of interest between your desire and what your family member wants?

How often have you had to change your own life and interests to fit around the need of your family member?

How often is caring physically demanding on you?

How often do you feel burdened by the demands of your family member?

Questions are asked by the relational agent and responses that may be in the form of YES/NO answers from patients or caregivers are recorded and processed by one or more skills. Responses may be assigned a numerical value, for example YES=1 and NO=0. A high sum of YES in this case provides a measure of non-adherence. In this example, the relational agent, based on the total score, might invoke another skill, a skill that provides a caregiver with coping skills. One of ordinary skill in the art can appreciate the novelty and usefulness of using the relational agent of the present invention; a voice-controlled speech recognition and natural language processing combined with the utility of validated clinical questionnaire scales. The combination of these modalities may be more conducive to eliciting information, providing feedback, and actively engaging patients and caregivers to support patient memory, social contact, daily activities, patient safety, support for caregivers, and provide feedback communication to healthcare providers in the management of neurocognitive and neurodegenerative conditions, syndromes, and diseases including dementia and AD.

A scale may be modifiable with variable number of items and may contain sub-scales with either YES/NO answers, or response options, response options assigned to number values, Likert-response options, or Visual Analog Scale (VAS) responses. VAS responses may be displayed via mobile app in the form of text messages employing emojis, digital images, icons, or the like.

The results from one or more scales may be obtained and or combined to monitor and provide support for patient memory, social contact, daily activities, patient safety, support for caregivers, and feedback communication for healthcare providers in the management of neurocognitive and neurodegenerative conditions, syndromes, and diseases including dementia and AD. Scales may be directed to either caregivers or PwD including scales relating to cognition, staging, function, delirium, QoL, or the like. The answers provided to the relational agent serve as input to one or more indices, predictive algorithms, statistical analyses, or the like, to calculate a risk stratification profile. Such a profile can provide an assessment for the need of any intervention required by either the patient, healthcare providers, caregivers, or family members. Additionally, when the system detects that a user, namely a patient with dementia, consistently performs poorly on activities targeting a specific cognitive function, then these activities could increasingly be presented to stimulate the user's cognitive function in a targeted way.

In summary, the pervasive integrated assistive technology system of this invention enables a high level of interaction for PwD, healthcare providers, caregivers, and family members. The system leverages a voice-activated empathetic relational agent to provide support of patient memory, social contact, daily activities, patient safety, support for caregivers, and feedback communication for healthcare providers. For PwD, the system supports the needs, but not limited to, memory function, activities of daily living, psychosocial behavior, orientation, safety, care, and information. For caregivers, the system supports the needs, but not limited to, information about PwD and their safety, advice and emotional support, and disease information resources. For healthcare providers, the system supports the needs, but not limited to, patient behavior, patient functional capacity, profile, medication adherence, routine adherence, and patient health status. The system has utility in the management of neurocognitive and neurodegenerative conditions, syndromes, and diseases including dementia and AD.

Example

This example is intended to serve as a demonstration of the possible voice interactions between a relational agent and a patient with dementia. The relational agent uses a control service (e.g., Amazon Lex, available from Amazon.com, Seattle, Wash.). Access to skills require the use of a device wake word (e.g., "Alexa") as well as an invocation phrase (e.g., "Wellnest") for skills specifically developed for a proprietary wearable device that embodies one or more components of the present disclosure. The following highlight one or more contemplated capabilities and uses of the invention:

| Feature | Sample Phrases |
|---|---|
| Onboarding Demo | "Alexa, open Wellnest" (conversation will continue) |
| Uber Ride Summoning | "Alexa, tell Wellnest I need an Uber" |
| | "Alexa, ask Wellnest to call a cab" |
| | "Alexa, ask Wellnest to take me somewhere" |
| Checking Messages | "Alexa, ask Wellnest if I have any messages" |
| | "Alexa, tell Wellnest to check my messages" |
| Appointment Schedule | "Alexa, ask Wellnest when my next appointment is." |
| | "Alexa, ask Wellnest about my appointment schedule." |
| Fire TV Video Content | "Alexa, ask Wellnest what is new on Fire TV" |
| | "Alexa, ask Wellnest if there is anything new on Fire TV" |
| Hair Styling Services | "Alexa, ask Wellnest where I can get my hair cut" |
| | "Alexa, ask Wellnest who can cut my hair" (conversation will continue) |
| Home Repair Services | "Alexa, tell Wellnest I need a handyman" |
| | "Alexa, ask Wellnest where I can get a repairman" |
| Device Battery | "Alexa, ask Wellnest how much battery is left" |

-continued

| Feature | Sample Phrases |
|---|---|
| Life | "Alexa, ask Wellnest how full my battery |
| Location Assistance | "Alexa, ask Wellnest where I am" |
| Identity Assistance | "Alexa, ask Wellnest what my name is" |
| | "Alexa, ask Wellnest who I am" |
| General Help | "Alexa, tell Wellnest I need help" |
| | "Alexa, ask Wellnest for help" (conversation will continue) |
| Emergency Assistance | "Alexa, tell Wellnest to call 911" |
| | "Alexa, ask Wellnest to call an ambulance" |
| Contact Family | "Alexa, tell Wellnest to call Hannah" |
| Medication Reminders | "Alexa, tell Wellnest it's morning" |
| | "Alexa, tell Wellnest it's midday" |
| | "Alexa, tell Wellnest it's evening" |
| Medication Adherence Measure | "Alexa, tell Wellnest I'd like to ask how I am doing with my medication" |

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system for management of neurocognitive and neurodegenerative conditions, syndromes, and diseases comprising:
 a speech interface device operably engaged with a communications network, the speech interface device being configured to receive a voice input from a patient user of the speech interface device, process a voice transmission from the voice input, and communicate the voice transmission over the communications network via at least one communications protocol, wherein the speech interface device has at least one audio output means, and the patient user of the speech interface device is a patient having a neurocognitive or neurodegenerative condition, syndrome, or disease; and,
 a remote server operably engaged with the speech interface device via the communications network to receive the voice transmission, the remote server executing a control service comprising an automated speech recognition function, a natural-language processing function, and one or more application protocols, the control service processing the voice transmission to execute one or more system commands, the one or more system commands comprising communicating an interaction of the patient user to the speech interface device, determining a health status of the patient user, fulfilling a request of the patient user, and communicating with one or more third-party servers, wherein:
 the control service executing on the remote server serves as a relational agent that provides conversational interactions with the patient user based on the automated speech recognition function, the natural-language processing function, and the one or more application protocols, the conversational interactions being directed to the management of neurocognitive and neurodegenerative conditions, syndromes, and diseases of the patient user; and the remote server comprises an application software comprising instructions for a user management function and a patient treatment function, the user management function being operable to define roles and permissions between the patient user and one or more non-patient users, and the patient treatment function being operable to perform one or more patient care protocols associated with the control service, the one or more patient care protocols comprising functions to perform non-pharmacologic interventions, wherein, in response to a command by the remote server, the relational agent further provides suggestions for non-pharmacologic interventions as corrective actions in the management of neurocognitive and neurodegenerative conditions, syndromes, and diseases, and wherein in response to a command by the remote server, the speech interface device communicates the suggested non-pharmacologic interventions to the patient user.

2. The system of claim 1 wherein the one or more patient care protocols further comprise instructions for tracking a location of the patient user, monitoring medication adherence of the patient user, and storing and tracking health data of the patient user.

3. The system of claim 1 wherein the application software is further operable to evaluate a degree of cognitive impairment in the patient user in response to the voice input by the patient user.

4. The system of claim 1 wherein the speech interface device further comprises a fall detection sensor and a GPS chipset, the speech interface device communicating a location and movement data of the patient user to the remote server at predetermined intervals.

5. The system of claim 1 wherein the application software further comprises instructions for providing a graphical user interface comprising a plurality of patient health data to an authenticated non-patient user device.

6. The system of claim 1 wherein the speech interface device communicates an audible cognitive stimulation or social function prompt to the patient user in response to a command by the remote server.

7. The system of claim 2 wherein the remote server is operable to alert an emergency service or one or more non-patient users in response to the one or more patient care protocols.

8. The system of claim 1 wherein the speech interface device is configured to enable the patient user to access and interact with the relational agent so as to support memory, social contact, daily activities, and safety of the patient user.

9. The system of claim 8 wherein information generated from the interaction of the patient user with the relational agent is stored in the remote server and incorporated into the application software.

10. A system for management of neurocognitive and neurodegenerative conditions, syndromes, and diseases comprising:

a patient interface device operably engaged with a communications network, the patient interface device being configured to receive a voice input from a patient user of the patient interface device, process a voice transmission from the voice input, and communicate the voice transmission over the communications network via at least one communications protocol, the patient interface device having at least one audio output means;

a remote server operably engaged with the patient interface device via the communications network to receive the voice transmission, the remote server executing a control service comprising an automated speech recognition function, a natural-language processing function, and one or more application protocols, the control service processing the voice transmission to execute one or more system commands, the one or more system commands comprising communicating an interaction prompt of the patient user to the patient interface device, determining a health status of the patient user, fulfilling a request of the patient user, and communicating with one or more third-party servers, wherein the control service executing on the remote server serves as a relational agent that provides conversational interactions with the patient user based on the automated speech recognition function, the natural-language processing function, and the one or more application protocols, the conversational interactions being directed to the management of neurocognitive and neurodegenerative conditions, syndromes, and diseases of the patient user; and a non-patient interface device operably engaged with the remote server via the communications network to receive the health status and communications associated with the patient user, the non-patient interface device being operable to configure one or more patient care protocols associated with the control service and send the communications to the patient interface device, the one or more patient care protocols comprising functions to perform or teach non-pharmacologic interventions, wherein the remote server comprises an application software comprising instructions for a user management function and a patient treatment function, the user management function being operable to define roles and permissions between the patient user of the patient interface device and one or more non-patient users of the non-patient interface device, and the patient treatment function being operable to perform or teach the one or more patient care protocols associated with the control service, wherein, in response to a command by the remote server, the relational agent provides suggestions for non-pharmacologic interventions as corrective actions in the management of neurocognitive and neurodegenerative conditions, syndromes, and diseases, and wherein, in response to a command by the remote server, the patient interface device communicates the suggested non-pharmacologic interventions to the patient user.

11. The system of claim 10 wherein the remote server is operably engaged with an electronic health server or a medical record server via an application programming interface.

12. The system of claim 10 further comprising a multimedia device communicably engaged with the remote server via the communications network, the multimedia device being configured to display a graphical user interface comprising a plurality of patient health data and historical data.

13. The system of claim 10 wherein the one or more patient care protocols further comprise functions for predicting patient behaviors.

14. The system of claim 10 wherein the one or more patient care protocols further comprise functions for monitoring patient compliance.

15. The system of claim 10 wherein the patient interface device is configured to enable the patient user to access and interact with the relational agent so as to support memory, social contact, daily activities, and safety of the patient user, and wherein information generated from the interaction of the patient user with the relational agent is stored in the remote server and incorporated into the application software.

16. A pervasive integrated assistive technology system for enabling a distributed care ecosystem for patients with neurocognitive conditions, comprising:
   a patient interface device operably engaged with a communications network, the patient interface device being configured to receive a voice input from a patient user, process a voice transmission from the voice input, and communicate the voice transmission over the communications network via at least one communications protocol, the patient interface device having at least one audio output means;
   a remote server operably engaged with the patient interface device via the communications network to receive the voice transmission, the remote server executing a control service comprising an automated speech recognition function, a natural-language processing function, and one or more application functions, the control service processing the voice transmission to execute one or more system commands, the one or more system commands comprising communicating an interaction prompt of the patient user to the patient interface device, determining a health status of the patient user, and fulfilling a request of the patient user,
      wherein the control service executing on the remote server serves as a relational agent that provides conversational interactions with the patient user based on the automated speech recognition function, the natural-language processing function, and the one or more application protocols, the conversational interactions being directed to the management of neurocognitive and neurodegenerative conditions, syndromes, and diseases of the patient user;
   a caregiver interface device operably engaged with the remote server via the communications network, the caregiver interface device being configured to receive the health status and communications associated with the patient user, and operable to configure one or more patient care protocols associated with the control service and send one or more of the communications to the patient interface device; and,
   a health care provider interface device operably engaged with the remote server via the communications network, the health care provider interface device being configured to receive the health status and communications associated with the patient user, and operable to configure the one or more patient care protocols associated with the control service and send one or more of the communications to the patient interface device and the caregiver interface device, wherein:
      in response to a command by the remote server, the relational agent further provides suggestions for non-pharmacologic interventions as corrective actions in the management of neurocognitive and neurodegenerative conditions, syndromes, and diseases; and
      in response to a command by the remote server, the patient interface device communicates the suggested non-pharmacologic interventions to the patient user.

17. The system of claim 16 wherein the remote server further comprises an application software comprising instructions for a user management module, a patient treatment module, a caregiver module, and a health care provider module.

18. The system of claim 17 wherein the caregiver module comprises instructions for delivering a quality of life assessment to a caregiver user.

19. The system of claim 17 wherein the health care provider module comprises instructions for monitoring patient health status and treatment adherence.

20. The system of claim 17 wherein:
   the user management module comprises instructions for defining roles and permissions between the patient user of the patient interface device and one or more non-patient users of the caregiver interface device and the health care provider interface device; and
   the patient treatment module comprises instructions for performing one or more patient care protocols associated with the control service.

* * * * *